(12) United States Patent
Haik

(10) Patent No.: US 9,005,582 B2
(45) Date of Patent: Apr. 14, 2015

(54) HYPERTHERMIA THERAPEUTIC AGENT DELIVERY SYSTEM

(71) Applicant: University of North Carolina at Greensboro, Greensboro, NC (US)

(72) Inventor: Yousef Haik, Al Ain (AE)

(73) Assignees: University of North Carolina at Greensboro, Greensboro, NC (US); United Arab Emirates University, Al Ain (AE)

( * ) Notice: Subject to any disclaimer, the term of this patent is extended or adjusted under 35 U.S.C. 154(b) by 0 days.

(21) Appl. No.: 13/722,850

(22) Filed: Dec. 20, 2012

(65) Prior Publication Data
US 2013/0129630 A1    May 23, 2013

Related U.S. Application Data

(62) Division of application No. 12/205,623, filed on Sep. 5, 2008, now abandoned.

(60) Provisional application No. 60/970,566, filed on Sep. 7, 2007, provisional application No. 60/971,286, filed on Sep. 11, 2007, provisional application No. 61/027,449, filed on Feb. 9, 2008.

(51) Int. Cl.
| | |
|---|---|
| A61K 47/48 | (2006.01) |
| A61K 35/74 | (2006.01) |
| A61K 41/00 | (2006.01) |
| A61K 49/18 | (2006.01) |
| B82Y 5/00 | (2011.01) |

(52) U.S. Cl.
CPC ....... *A61K 47/48853* (2013.01); *A61K 41/0052* (2013.01); *A61K 49/1851* (2013.01); *B82Y 5/00* (2013.01)

(58) Field of Classification Search
USPC ........... 424/9.321, 9.323, 9.32, 9.1, 9.6, 1.11, 424/617, 641, 646
See application file for complete search history.

(56) References Cited

U.S. PATENT DOCUMENTS

| 6,514,418 B1 | 2/2003 | Bartscherer et al. | |
|---|---|---|---|
| 7,074,175 B2 | 7/2006 | Handy et al. | |
| 2004/0234455 A1* | 11/2004 | Szalay | 424/9.6 |
| 2005/0249817 A1* | 11/2005 | Haik et al. | 424/617 |

* cited by examiner

*Primary Examiner* — Michael G Hartley
*Assistant Examiner* — Jagadishwar Samala
(74) *Attorney, Agent, or Firm* — Akerman LLP; Michael K. Dixon

(57) ABSTRACT

A medical delivery system that enables the delivery of therapeutic agents to malignant tissue utilizing delivery agents and heating of the delivery agents thereby causing the release of the therapeutic agents within the tumor is disclosed. The therapeutic agents may be chemotherapy agents, radiation therapy agents, and other appropriate materials. The magnetic nanoparticles encapsulated by the therapeutic agents in a biocompatible coating may be delivered to tumor sites utilizing attenuated strains of bacteria that seek and reside at tumor sites. An alternating magnetic field device with a prescribed frequency range may be used to induce heating of the magnetic nanoparticles in the patient thereby melting the coating and releasing the therapeutic agents within the tumor.

9 Claims, 6 Drawing Sheets

HYPERTHERMIA THERAPEUTIC AGENT DELIVERY SYSTEM

CROSS-REFERENCE TO RELATED APPLICATION

This application is a divisional of U.S. patent application Ser. No. 12/205,623, filed Sep. 5, 2008, which claims the benefit of U.S. Provisional Patent Application No. 60/970,566, filed Sep. 7, 2007, U.S. Provisional Patent Application No. 60/971,286, filed Sep. 11, 2007 and U.S. Provisional Patent Application No. 61/027,449, filed Feb. 9, 2008, all of which are incorporated by reference.

FIELD OF THE INVENTION

This invention is directed to a therapeutic agent delivery system, and more particularly, to a therapeutic agent delivery system that enables a therapeutic agent to be delivered safely to a tumor via a bloodstream and released within the tumor when exposed to an alternating magnetic field.

BACKGROUND OF THE INVENTION

Reports of advances in the creation of therapeutic agents for cancer treatment have increased in recent years. Nevertheless, the ability to localize chemotherapy agents at the tumor sites has been hindered by adverse toxicity to the normal tissue. The challenges of enforcing residence of the drug carriers at the tumor site have not been efficiently met by the existing technology. Additionally, the inability to control the release of drugs while at the tumor site is a major reason for the lack of efficiency of existing targeted drug delivery systems.

Heating organs and tissues as a treatment of cancer is well known. The first reference to link heat and the destruction of cancerous growths was as early as 3000 BC in the contents of an Egyptian papyrus and later in the writings of Hippocrates. More scientifically, the connection between disappearance of tumors and high fever, either from infections or artificially induced by bacterial toxins, have initiated a concept of thermotherapy. Reports on enhanced selective thermal sensitivity of animal tumors compared with normal tissue confirm that hyperthermia may be considered as a cytotoxic agent. There has been work conducted on many aspects of heat application to tumors, which has lead to rapid development in therapeutic applicator design and to the increased sophistication of hyperthermia equipment.

Hyperthermic temperatures increase blood circulation in tumors. The increase in temperature increases the presence of oxygen-bearing blood in tumor tissues, which is critical for increasing the effectiveness of ionizing radiation. Ionizing radiation, also referred to as radiotherapy, destroys tumor cells substantially through the formation of oxygen radicals that attack the cell DNA of a tumor. Oxygen-starved cells are three-times more resistant to ionizing radiation than are normal cells. Low oxygen levels in human tumors, referred to as hypoxia, have been linked to failure in achieving local tumor control through ionizing radiation. In addition, the degree of oxygen deficiency in cancerous tumors is a key predictor of the efficacy of ionizing radiation therapy. Results from molecular biology research demonstrate that hyperthermia treatments may be used in many different tumors particularly for local tumor control. Such hyperthermia treatments resulted in an increase in the survival rate of the patients, especially when hyperthermia was combined with radiation therapy.

SUMMARY OF THE INVENTION

This invention is directed to a therapeutic agent delivery system and a delivery agent having a biocompatible coating with a therapeutic agent that is configured to readily enter and reside in a tumor within a living being, such as a human or animal. The delivery agent may be attached to an attenuated bacteria strain that is readily taken up by tumors within a living being. The delivery agent may be subjected to an alternating magnetic field device with a prescribed frequency range to induce heating of the magnetic nanoparticles in the patient thereby melting the coating and releasing the therapeutic agents within the tumor. By releasing the therapeutic agents directly into the tumor, the problems associated with resistance to chemotherapy and radiation therapy by hypoxic cells is eliminated. Thus, whether cells are hypoxic or euoxic does not affect the ability of a tumor to be treated with chemotherapy or radiation therapy, or both.

The delivery agent may be formed from one or more magnetic nanoparticles having a Curie temperature less than a critical temperature of tissue at which the tissue is compromised. The Curie temperature of the magnetic nanoparticle may be less than 44° C., such as between about 40° C. and about 44° C. The delivery agent may be coated with a biocompatible, thermosensitive coating including at least one therapeutic agent encapsulating the at least one magnetic nanoparticle. The biocompatible, thermosensitive coating may melt when exposed to heat, thereby releasing the at least one therapeutic substance into the tumor. The therapeutic agent may be a chemotherapy agent, a radiation therapy agent, or another appropriate material.

The encapsulated delivery agent may be attached to an attenuated bacteria strain. In particular, the encapsulated delivery agent may be uploaded to an attenuated bacteria strain, such as, but not limited to, *Salmonella*. The bacteria strain with the encapsulated delivery agent may readily enter and reside in a tumor within a living being, such as a human or animal, when placed into a bloodstream of the living being. Utilizing attenuated bacteria as a carrier overcomes the issues associated with tagging and delivering conventional delivery agents to a site of interest such as a tumor. Genetically modified strains of bacteria, such as, *Salmonella typhimurium*, have been shown to accumulate at tumor sites when injected in tumor-bearing mice and clear rapidly from blood in normal mice. The innovative delivery system makes use of genetically modified strains of bacteria, which includes genetically stable attenuated virulence (deletion of purI gene), reduction of septic shock potential (deletion of msbB gene) and antibiotic susceptibility.

The delivery agents may be delivered to tumors within a patient with a delivery system in which the at least one magnetic nanoparticle is encapsulated with a biocompatible coating having a therapeutic agent and is attached to an attenuated bacteria strain. In particular, the magnetic nanoparticles may be uploaded to attenuated bacteria strains. The predetermined concentration of bacteria may be placed, through injection or otherwise, into a bloodstream of a patient, such as a human being or animal, to identify tumors within the patient. Once in the bloodstream, the bacteria seeks out the tumor. Once the bacteria locates the tumor, the bacteria enters the tumor and resides therein. If no tumor is present, the attenuated bacteria strains are passed out of the patient within 24 hours of being injected into the patient.

An alternating magnetic field may then be applied in proximity of the tumor location 24 hours after administering the loaded bacteria to the patient. The alternating magnetic field induce heating within the magnetic nanoparticles and melt the biocompatible coating, thereby releasing the therapeutic agent into the tumor. In embodiments where the delivery agents are those having a Curie temperature less than a critical temperature of tissue at which the tissue is compromised, the magnetic nanoparticles when subjected to the alternating magnetic field heat up to a predetermined Curie temperature and do not increase in temperature beyond the Curie temperature.

An advantage of this invention is that the ability to deliver chemotherapy agents and radiation therapy agents to a tumor is not affected by whether the cells forming the tumor are hypoxic or euoxic.

Another advantage with this invention is that the delivery agents may be attached to bacteria strains that are readily taken up by tumors, thereby forming a delivery mechanism that effectively delivers that delivery agents to a tumor such that the tumor may be easily identified by a concentration of delivery agents therein.

Yet another advantage of this invention is that the delivery agents heat up due to exposure to an alternating magnetic current to a temperature below a temperature at which damage can occur to surrounding tissue.

Another advantage of this invention is that the delivery system reduces the risk of inducing a toxic reaction at normal sites because the delivery system does not use toxic materials, which were used in conventional systems.

Still another advantage is that the magnetic nanoparticles are synthesized with biocompatible components so that the magnetic nanoparticles can be administered to a tumor without causing toxic reaction to normal tissue and can be activated once at the tumor site utilizing a noninvasive alternating magnetic field, thereby combining hyperthermia with other modalities, which increases the treatment benefits.

These and other embodiments are described in more detail below.

BRIEF DESCRIPTION OF THE DRAWINGS

The accompanying drawings, which are incorporated in and form a part of the specification, illustrate embodiments of the presently disclosed invention and, together with the description, disclose the principles of the invention.

DETAILED DESCRIPTION OF THE INVENTION

As shown in FIGS. 1-11, the invention is directed to a delivery system and a delivery agent having a biocompatible coating with a therapeutic agent that is configured to readily enter and reside in a tumor within a living being, such as a human or animal. The delivery agent may be attached to an attenuated bacteria strain that is readily taken up by tumors within a living being. The delivery agent may be subjected to an alternating magnetic field device with a prescribed frequency range to induce heating of the magnetic nanoparticles in the patient thereby melting the coating and releasing the therapeutic agents within the tumor.

Figure 1:
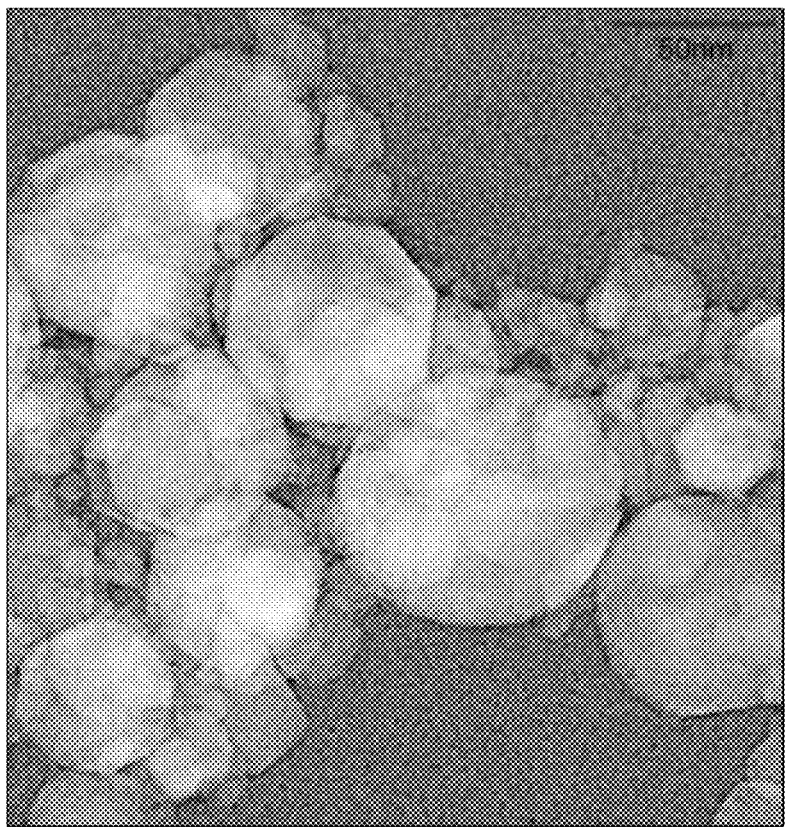
FIG. 1 is a transmission electron microscopy image of a thermosensitive polymer encapsulating a biocompatible self-controlled magnetic nanoparticle along with a therapeutic agent.

In one embodiment, the delivery agent may be formed from one or more magnetic nanoparticles, as shown in FIG. 1, having a Curie temperature less than a critical temperature of tissue at which the tissue is compromised such that the delivery agent may be heated to a temperature not to exceed the Curie temperature, thereby preventing damage to the surrounding tissue. A delivery system for a delivery agent for use in imaging systems is disclosed in which the magnetic nanoparticle having a Curie temperature less than a critical temperature of the tissue is placed in contact with a carrier that is an attenuated bacteria strain to facilitate uptake of the delivery agent by a tumor.

The magnetic nanoparticles may be formed from particles having cross-sections between five nm to less than one micron in width. In other embodiment, the magnetic nanoparticles may be larger particles. As used herein, the term "magnetic nanoparticles" includes magnetic, paramagnetic, superparamagnetic ferromagnetic and ferrimagnetic materials. The nanoparticles may be formed from a combination of magnetic and nonmagnetic materials. Such combinations may be configured to have a Curie temperature between about 40° C. and about 44° C. As such, when the magnetic nanoparticles are excited by an alternating magnetic field, the magnetic nanoparticles experience a temperature rise up to, but not exceeding, their Curie temperature. The magnetic nanoparticles may be synthesized using chemical or physical methods. For instance, the magnetic nanoparticles may be formed from materials, such as, but not limited to, CuNi (binary nanoparticle), MnGdFe, ZnGdFe, FeGdB, FeNdB (tri nanoparticles) or MnZnGdFe (quad nanoparticles).

Figure 5A:
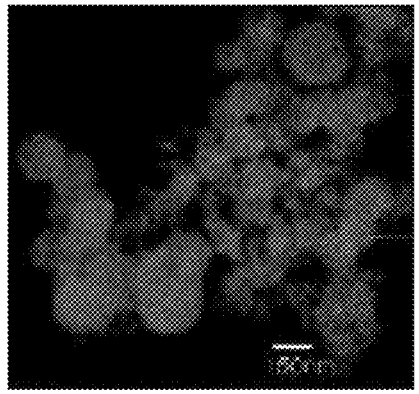
FIGS. 5A-C are TEM micrographs for three difference FNB compositions that are referred to as (A) TEM for FNB1, (B) TEM for FNB2 and (C) TEM for FNB3.
Figure 5B:
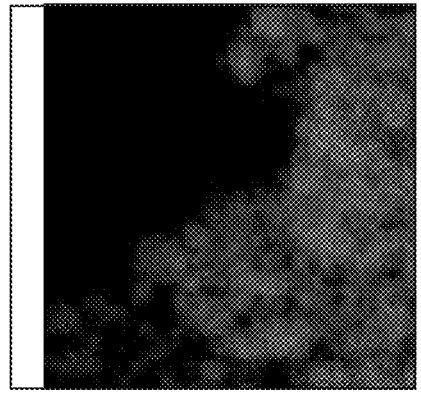
Figure 5C:
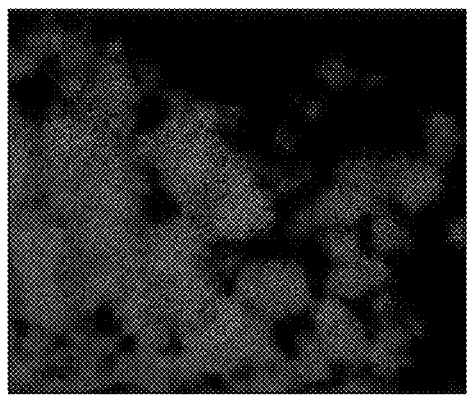
Figure 6:
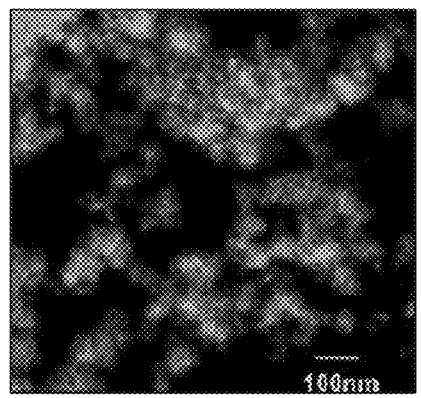
FIG. 6 is an image of silica coated particles.
Figure 7:
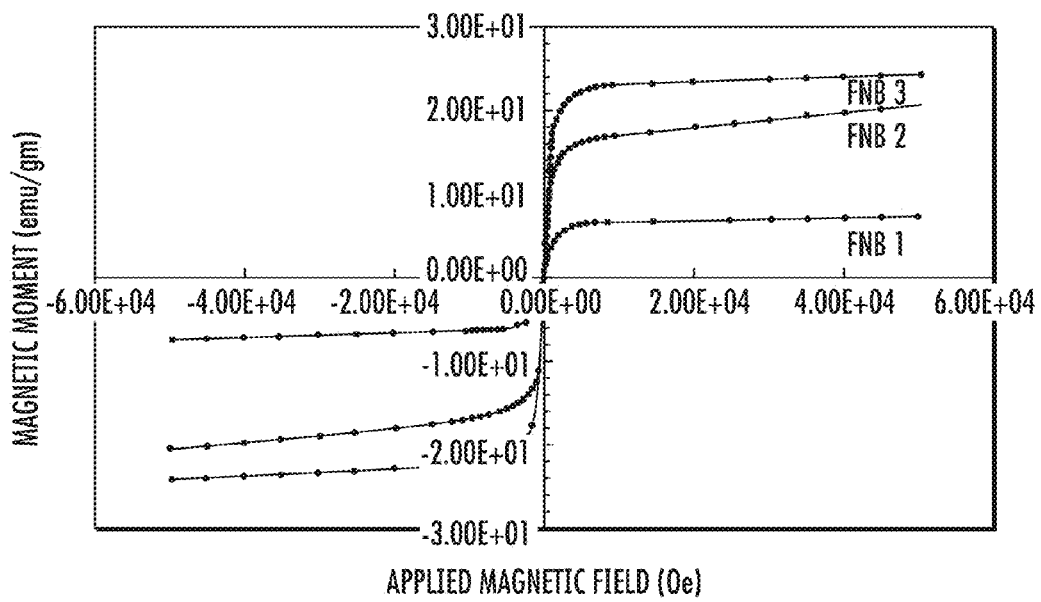
FIG. 7 is graph of an applied magnetic field vs. magnetization plot.
Figure 8:
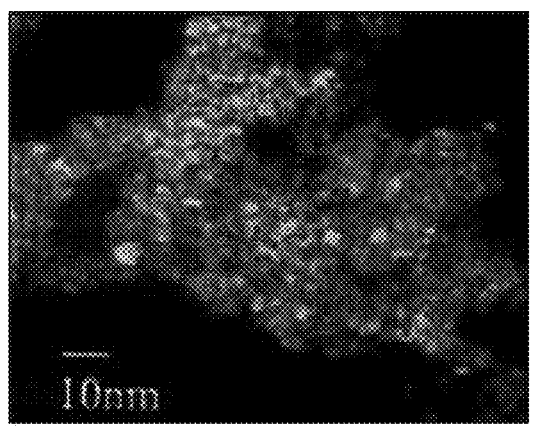
FIG. 8 is an image of iron oxide particles.
Figure 9:
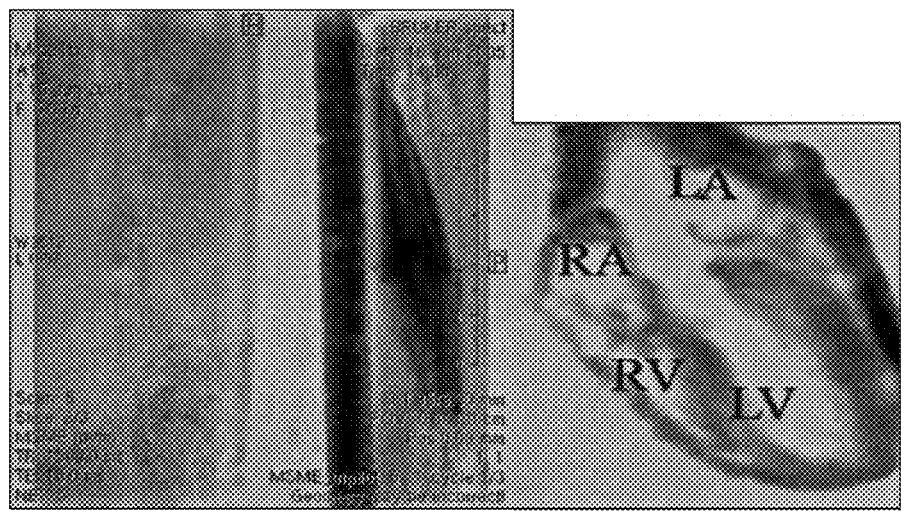
FIG. 9 is a MRI of a patient with iron oxide delivery agent.

The magnetic nanoparticles may be formed using co-precipitation method and borohydride reduction method. For example, FeGdB and FeNdB nanoparticles have been synthesized using a borohydride reduction method. Ultrasonication was used to form homogeneously sized particles in the nanometer range (30-100 nm). In order to minimize the oxidation effect, these particles were passivated overnight under a continuous flow of oxygen and nitrogen. These particles were further coated with silica by using a precipitation process and have been designed for biomedical applications. Silica coated particles are capable of chemically attaching to proteins and many other biological molecules. Morphology and sizes of all of the magnetic nanoparticles were determined with scanning transmission electron microscopy (TEM). The magnetic properties of the magnetic nanoparticles were studied using a Superconducting Quantum Interference Device (SQUID) magnetometer. The composition of the alloy material was determined by inductively coupled plasma atomic emission spectroscopy (ICP). The ICP analysis of magnetic nanoparticles identified the stoicheometric composition of three alloys as $Fe_{5.6}NdB_2$, $Fe_{5.4}NdB_9$ and $Fe_{5.2}NdB_{13.7}$. For the purpose of discussion, the samples are designated as FNB1, FNB2 and FNB3 respectively. The composition of the alloy is strongly dependent on the reaction conditions. FIGS. 5A, 5B and 5C show the TEM micrograph for FNB 1, FNB2 and FNB 3, respectively. The magnetic nanoparticles are mostly in the size range of between 50 nm and 200 nm. FIG. 6 shows an image of silica coated FeNdB particles. The micrograph depicts that the cluster of the magnetic nanoparticles rather than individual particles have been coated with silica. The hysterics plots shown in FIG. 8 at 300K indicate the superparamagnetic nature of all samples as there was almost no remnant magnetization.

In at least one embodiment, the magnetic nanoparticles may be encapsulated by one or more biocompatible coatings. The encapsulated delivery agents may have a cross-section between about 10 nm and one micron. The biocompatible coating may be, but are not limited to, a polymeric material, a biodegradable material, and a protein. A polymeric material may be, but is not limited to, one or more oligomers, polymers, copolymers, or blends thereof. Examples of polymers include polyvinyl alcohol; polyethylene glycol; ethyl cellulose; polyolefins; polyesters; nonpeptide polyamines; polyamides; polycarbonates; polyalkenes; polyvinyl ethers; polyglycolides; cellulose ethers; polyvinyl halides; polyhydroxyalkanoates; polyanhydrides; polystyrenes; polyacrylates, polymethacrylates; polyurethanes; polypropylene; polybutylene terephthalate; polyethylene terephthalate; nylon 6; nylon 6,6; nylon 4,6; nylon 12; phenolic resins; urea resins; epoxy resins; silicone polymers; polycarbonates; polyethylene vinylacetate; polyethylene ethyl acrylate; polylactic acid; polysaccharides; polytetrafluoroethylene; polysulfones and copolymers and blends thereof. The polymeric material may be biocompatible and may be biodegradable. Examples of suitable polymers include ethylcelluloses, polystyrenes, poly(ε-caprolactone), poly(d,l-lactic acid), polysaccharides, and poly(d,l-lactic acid-co-glycolic acid). The polymer may be a copolymer of lactic acid and glycolic acid (e.g., PLGA). The protein may be, but is not limited to, BSA or HSA.

Figure 2:
FIG. 2 is an image of the attenuated bacteria strain with encapsulated therapeutic agents.

The delivery agents may also include one or more therapeutic agents included within the biocompatible coating, as shown in FIG. 2. The therapeutic agent may be a chemotherapy agent, a radiation therapy agent, such as, a radiation sensitizer, or other appropriate material. The therapeutic agent may be included in the biocompatible coating surrounding the delivery agent.

The biocompatible coating may have a melting temperature that is less than a Curie temperature for the delivery agents. When heated the biocompatible coating may melt and release the therapeutic agent. In one embodiment, a solution to be administered to a patient may be formed in which the delivery agents may include different therapeutic agents or differing amounts of a therapeutic agent. In particular, one or more first the delivery agents may include a first therapeutic agent in a biocompatible coating with a first melting point. In addition, one or more delivery agents may include a second therapeutic agent that is different from the first therapeutic agent in a biocompatible coating with a second melting point that is greater than the first melting point. In such an embodiment, the delivery agents may be delivered to target tissue. The target tissue and the delivery agents may be heated together up to the first temperature at which the biocompatible coating enclosing the first therapeutic agent melts, thereby releasing the first therapeutic agent. If it is determined that the second therapeutic agent should be released, the target tissue and the delivery agents may be heated to the second temperature to melt the biocompatible coating enclosing the second therapeutic agent, thereby releasing the second therapeutic agent. In an alternative embodiment, the second delivery agents may include a different amount of the first therapeutic agent, such as increased or reduced amounts of concentrations. The different amount of the first therapeutic agent may be released when desired.

In one embodiment, the delivery agents may be uploaded to attenuated bacteria strains to facilitate greater uptake by a tumor of the delivery agents. The attenuated bacteria strains may be genetically modified strains of bacteria, including genetically stable attenuated virulence (deletion of purl gene), reduction of septic shock potential (deletion of msbB gene) and antibiotic susceptibility. The delivery agents that are uploaded to the attenuated bacteria strains may be encapsulated by the biocompatible coating having one or more therapeutic agents.

Figure 10:
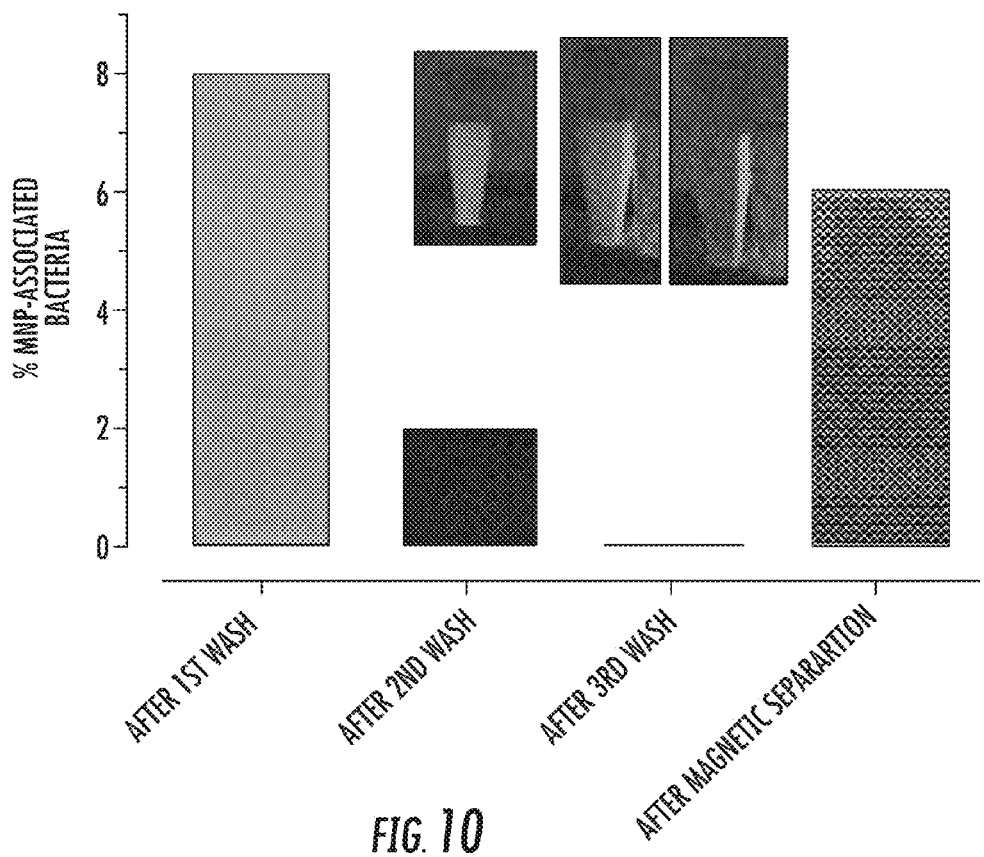
FIG. 10 is a graph of the uploading process of the magnetic nanoparticles to the bacteria.

The magnetic nanoparticles may be uploaded to attenuated bacteria strains via incubating the bacteria with the magnetic nanoparticles. For example, experiments were conducted in which magnetic nanoparticles ranging from 80-120 nm in size were utilized. As can be seen from Table 1, the conditions of incubating the bacteria with magnetic nanoparticles varied with respect to time (30 or 120 minutes) and temperature (4° C., 24° C., or 37° C.). In these experiments, $1 \times 10^8$ colony forming units (CFUs) of *Salmonella* strain BRD509 were incubated with magnetic nanoparticles in saline buffer. At the end of the incubation period, the bacterial suspension was spun down and the supernatant was aspirated. After resuspending the bacterial pellet in 1 ml saline, the bacterial suspension was subjected to a 0.45 Tesla permanent magnet for 15 minutes on the outside surface of the eppendorf tube, as shown in FIG. 10. The remaining supernatant, presumably containing bacteria without magnetic nanoparticles, was aspirated, and replaced with fresh saline. This procedure was repeated three times. Aliquots were removed from the bacterial suspension before and after each wash cycle and plated to determine the actual count of bacterial CFUs.

Using this procedure, the number of bacterial CFUs remaining after four cycles of magnetic separation and washing (which most likely represents the number of bacteria actually associated with magnetic nanoparticles) was determined, and hence the percentage of bacteria associated with the magnetic nanoparticles was calculated. The results of this analysis are summarized. FIG. 10 illustrates the loss of *Salmonella* organisms without magnetic nanoparticles, following co-incubation with magnetic nanoparticles at 24° C. for 120 minutes, after each cycle of wash. This demonstrates that all bacteria not associated with nanoparticles are effectively removed by the third wash cycle. Furthermore, as shown in the data in Table 1, varying the incubation conditions have a clear impact on the uptake of magnetic nanoparticles by the bacteria. Incubation of magnetic nanoparticles with live *Salmonella* organisms at room temperature resulted in uptake of about six percent ($6 \times 10^6$), which was sufficient for the loading purpose. The fact that the association appears to be strong suggests that it is feasible to use the *Salmonella* organisms loaded with magnetic nanoparticles in tumor-targeting in vivo.

TABLE 1

Relative efficiency of magnetic nanoparticle uptake by Salmonella under different incubation conditions.

| Incubation Conditions | | Percent of MNP |
|---|---|---|
| Time (minutes) | Temperature (° C.) | loaded with bacteria |
| 30 | 37 | 3.8% |
| 120 | 37 | 4.0% |
| 30 | 24 | 4.3% |
| 120 | 24 | 6.0% |
| 30 | 4 | 1.0% |
| 120 | 4 | 5.0% |

To show the preferential tropism of bacteria to tumor sites, a study was performed where mice previously implanted with B16F1 melanoma were treated with a single i.p. injection of either BRD509 or GIDIL2 strain of *Salmonella typhimurium*. On day seven post treatment, mice were sacrificed and tissue homogenates were prepared from tumor, liver, and mesenteric lymph nodes (MLN).

Figure 11:
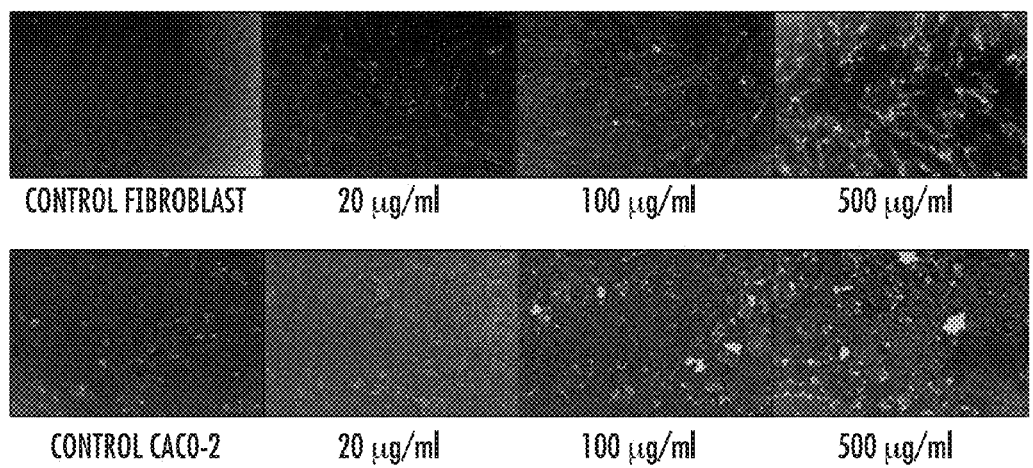
FIG. 11 is a comparison of images of different concentrations of cytotoxicity of fibroblast and caco-2.

The toxicity of the magnetic nanoparticles was investigated, and the experiments determined that the cell morphology did not change. In particular, magnetic nanoparticles were incubated with fibroblasts and Caco-2 cells lines for 24 hours to test their potential toxic effect on normal human and cancer human cells. Three different concentrations of magnetic nanoparticles were used in the experiment, and the cells were examined using light microscopy. Cell morphology of the normal human and cancer human cells remained unchanged during the entire incubation period. FIG. 11 shows the fibroblasts in the upper panel and Caco-2 cells in the lower panel. There was no toxic response observed for the bacteria incubated with magnetic nanoparticles.

During use, the delivery agents having a biocompatible coating with one or more therapeutic agents may be placed, through injection or otherwise, into a bloodstream of a patient, such as a human being or animal, to identify tumors within the patient. In particular, a predetermined concentration of bacteria loaded with delivery agents may be placed into a bloodstream feeding a tumor. Once in the bloodstream, the bacteria seeks the tumor. Once the bacteria locates the tumor, the bacteria enters the tumor and resides therein. If no tumor is present, the attenuated bacteria strains are passed out of the patient within 24 hours of being injected into the patient.

Figure 3:
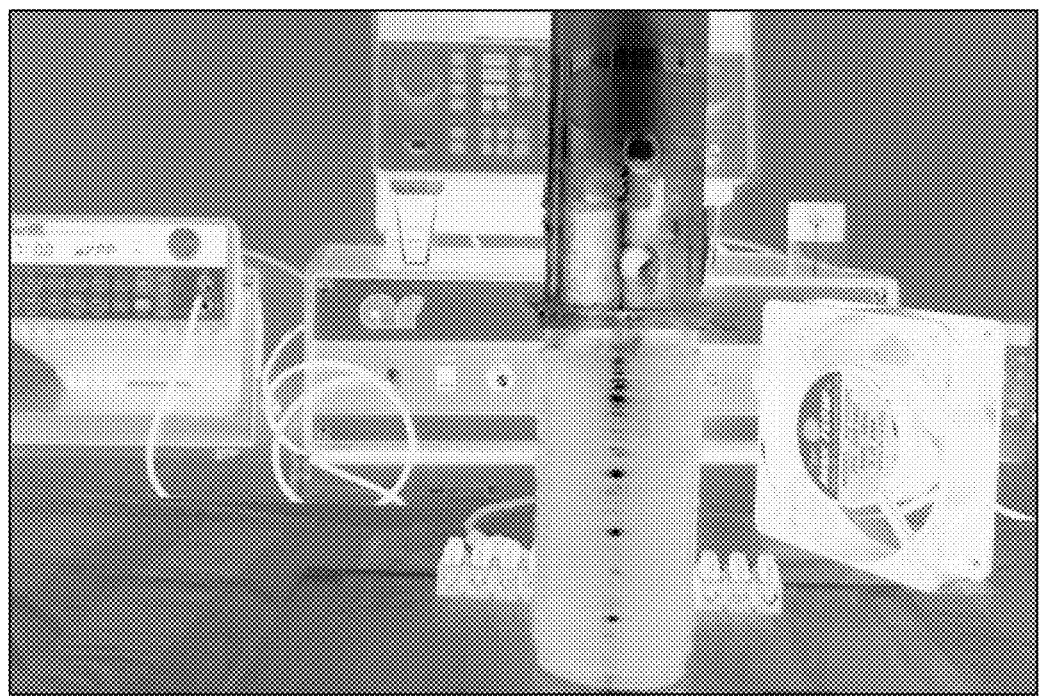
FIG. 3 is a perspective view of the alternating magnetic field generator.
Figure 4:
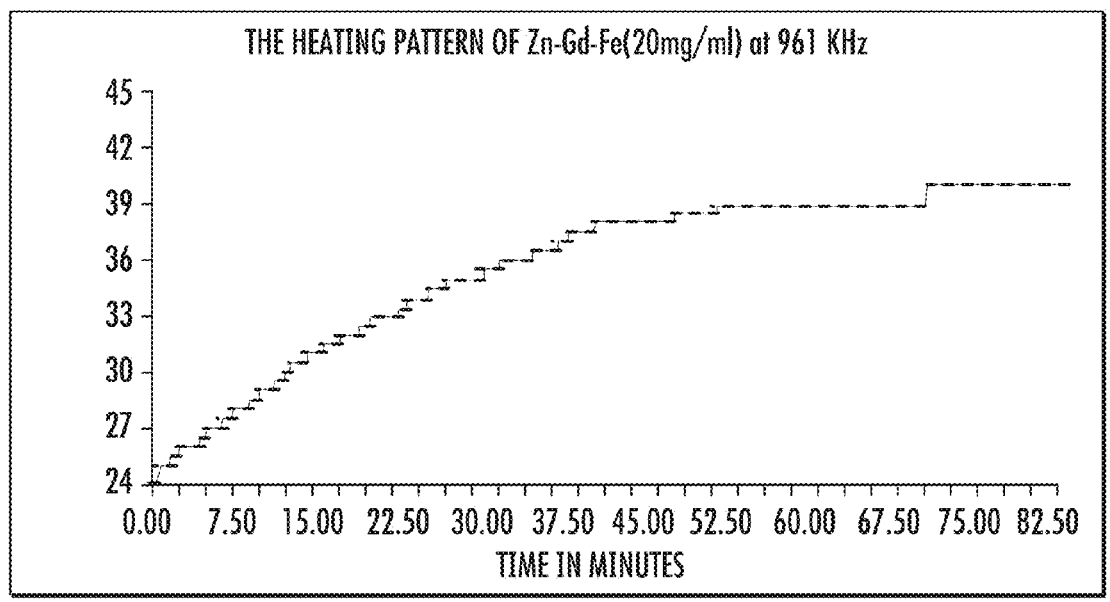
FIG. 4 is a diagram illustrating the self-controlled temperature rise when the hyperthermia agent is placed in an alternating magnetic field.

An alternating magnetic field may then be applied using a generator, such as the generator shown in FIG. 3, in proximity of the tumor location 24 hours after administering the loaded bacteria to the patient. The magnetic nanoparticles are heated within the tumor tissue. In embodiments where the delivery agents are those having a Curie temperature less than a critical temperature of tissue at which the tissue is compromised, the magnetic nanoparticles, when subjected to the alternating magnetic field, heat up to a predetermined Curie temperature and do not increase in temperature beyond the Curie temperature, as shown in FIG. 4. Heating the delivery agents having biocompatible coatings with one or more therapeutic agents causes the coating to melt and to release the therapeutic agents into the tumor. By releasing the therapeutic agents directly into the tumor, the problems associated with resistance to chemotherapy and radiation therapy by hypoxic cells is eliminated.

The foregoing is provided for purposes of illustrating, explaining, and describing embodiments of this invention. Modifications and adaptations to these embodiments will be apparent to those skilled in the art and may be made without departing from the scope or spirit of this invention.

I claim:

1. A delivery system for a delivery agent for use in imaging systems, comprising:
   at least one magnetic nanoparticle having a Curie temperature less than a critical temperature of tissue at which the tissue is compromised;
   a biocompatible, thermosensitive coating including at least one therapeutic agent encapsulating the at least one magnetic nanoparticle;
   wherein the biocompatible, thermosensitive coating melts when exposed to heat at or less than the Curie temperature, thereby releasing the at least one therapeutic agent;
   wherein the at least one magnetic nanoparticle is attached to an attenuated bacteria strain; and
   wherein the at least one magnetic nanoparticle has been attached to an outer surface of an attenuated bacteria strain via incubating the attenuated bacteria strain with the at least one magnetic nanoparticle.

2. The delivery system of claim 1, wherein the at least one magnetic nanoparticle comprises a combination of magnetic and nonmagnetic materials.

3. The delivery system of claim 1, wherein the at least one magnetic nanoparticle has a cross-sectional width of between five nm and one micron.

4. The delivery system of claim 1, wherein the Curie temperature is less than 44 degrees Celsius.

5. The delivery system of claim 1, wherein the attenuated bacteria strain is Salmonella typhimurium.

6. A method of administering a temperature dependent therapeutic material to a patient, comprising:
   administering at least one magnetic nanoparticle to a patient, wherein the at least one magnetic nanoparticle has a Curie temperature less than a critical temperature of tissue at which the tissue is compromised and wherein the at least one magnetic nanoparticle is at least partially encapsulated with a biocompatible, thermosensitive coating including at least one therapeutic agent encapsulating the at least one magnetic nanoparticle;
   subjecting the patient to a magnetic field, which causes the at least one magnetic nanoparticle to increase in temperature no higher than the Curie temperature and to melt the biocompatible, thermosensitive coating thereby releasing the at least one therapeutic agent
   wherein administering the at least one magnetic nanoparticle to a patient comprises administering at least one magnetic nanoparticle attached to an attenuated bacteria strain for increasing uptake by a tumor within the patient; and
   wherein the at least one magnetic nanoparticle has been attached to an outer surface of an attenuated bacteria strain via incubating the attenuated bacteria strain with the at least one magnetic nanoparticle.

7. The method of claim 6, wherein the at least one magnetic nanoparticle comprises a plurality of magnetic nanoparticles and at least one of the magnetic nanoparticles is coated at least partially with a biocompatible, thermosensitive coating including a first therapeutic agent whereby the coating melts at a first temperature, and another magnetic nanoparticle is coated at least partially with a biocompatible, thermosensitive coating including a second therapeutic agent differing from the first therapeutic agent whereby the coating melts at a second temperature that is greater than the first temperature enabling different therapeutic agents to be administered depending on temperature.

8. The method of claim 6, wherein the at least one magnetic nanoparticle comprises a plurality of magnetic nanoparticles and at least one of the magnetic nanoparticles is coated at least partially with a biocompatible, thermosensitive coating including a first therapeutic agent whereby the coating melts at a first temperature, and another magnetic nanoparticle is coated at least partially with a biocompatible, thermosensitive coating including a different amount of the first therapeutic agent differing from the first therapeutic agent whereby the coating melts at a second temperature that is greater than the first temperature enabling a different amount of therapeutic agents to be administered depending on temperature.

9. The method of claim 6, wherein administering the at least one magnetic nanoparticle to a patient comprises administering the at least one magnetic nanoparticle attached to an attenuated bacteria strain of Salmonella for increasing uptake by a tumor within the patient.

* * * * *